US00PP15280P2

(12) United States Plant Patent
Westhoff

(10) Patent No.: US PP15,280 P2
(45) Date of Patent: Oct. 26, 2004

(54) ***PETUNIA* PLANT NAMED 'WESPECAWHITE'**

(50) Latin Name: *Petunia×hybrida*
Varietal Denomination: Wespecawhite

(75) Inventor: Heinrich Westhoff, Südlohn (DE)

(73) Assignee: Josef & Heinrich Westhoff Gartenbau Spezialkulturen, Südlohm-Oeding (DE)

( * ) Notice: Subject to any disclaimer, the term of this patent is extended or adjusted under 35 U.S.C. 154(b) by 0 days.

(21) Appl. No.: 10/759,722

(22) Filed: Jan. 16, 2004

(51) Int. Cl.[7] ..... A01H 5/00
(52) U.S. Cl. ..... Plt./356
(58) Field of Search ..... Plt./356

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Petunia* plant named 'Wespecawhite', characterized by its cascading, roughly spherical growth habit; freely branching plant habit; freely flowering habit; small leaves; and single white-colored flowers with violet blush and purple-colored venation.

1 Drawing Sheet

Botanical classification/cultivar designation: *Petunia×hybrida* cultivar Wespecawhite.

BACKGROUND OF THE INVENTION

The present Invention relates to a new and distinct cultivar of *Petunia* plant, botanically known as *Petunia×hybrida,* and hereinafter referred to by the name 'Wespecawhite'.

The new *Petunia* is a product of a planned breeding program conducted by the Inventor is Südlohn-Oeding, Germany. The new *Petunia* originated from a cross-pollination made by the Inventor of a proprietary *Petunia* seedling selection, not patented, as the female, or seed parent, identified as code number 98K6384-340 with a proprietary *Petunia* seedling selection, not patented, as the male, or pollen, parent, identified as code number 98P040. The new *Petunia* was selected by the Inventor in 2000 in a controlled environment in Südlohn-Oeding, Germany.

Asexual reproduction of the new cultivar by terminal cuttings in Südlohn-Oeding, Germany since 2001, has shown that the unique features of this new *Petunia* are stable and reproduced true to type in successive generations.

SUMMARY OF THE INVENTION

Plants of the cultivar Wespecawhite have not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Wespecawhite'. These characteristics in combination distinguish 'Wespecawhite' as a new and distinct *Petunia* cultivar:

1. Cascading and roughly spherical growth habit.
2. Freely branching plant habit.
3. Freely flowering habit.
4. Small leaves.
5. Single white-colored flowers with violet-colored blush and purple-colored venation.

Plants of the new *Petunia* are more freely branching, have larger flowers, and have flowers of a different color than plants of the female parent. Plants of the new *Petunia* have smaller leaves, shorter internodes and smaller flowers than plants of the male parent.

Plants of the cultivar Wespecawhite can be compared to plants of the *Petunia* cultivar Wespemab, disclosed in U.S. Plant Pat. No. 14,165. However in side-by-side comparisons conducted in Südlohn-Oeding, Germany, plants of the new *Petunia* and the cultivar Wespemab, differed in the following characteristics:

1. Plants of the new *Petunia* were shorter than plants of the cultivar Wespemab.
2. Plants of the new *Petunia* had lighter green-colored leaves than plants of the cultivar Wespemab.
3. Plants of the new *Petunia* had leaves with shorter petioles than plants of the cultivar Wespemab.
4. Plants of the new *Petunia* had shorter sepals than plants of the cultivar Wespemab.
5. Plants of the new *Petunia* had longer peduncles than plants of the cultivar Wespemab.
6. Flower color of the new *Petunia* was different than flower color of the cultivar Wespemab.

Plants of the cultivar Wespecawhite can also be compared to plants of the *Petunia* cultivar Weswei, disclosed in U.S. Plant Pat. No. 11,595. However in side-by-side comparisons conducted in Südlohn-Oeding, Germany, plants of the new *Petunia* and the cultivar Weswei differed in the following characteristics:

1. Plants of the new *Petunia* had smaller leaves than plants of the cultivar Weswei.
2. Plants of the new *Petunia* had smaller sepals than plants of the cultivar Weswei.
3. Plants of the new *Petunia* had shorter peduncles than plants of the cultivar Weswei.
4. Flowers of the new *Petunia* were smaller than flowers of the cultivar Weswei.
5. Anthers of flowers of the new *Petunia* and the cultivar Weswei differed in coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which accurately describe the colors of the new *Petunia*.

The photograph at the top of the sheet comprises a side perspective view of a typical plant of 'Wespecawhite'.

The photograph at the bottom of the sheet comprises a close-up view of a typical flower of 'Wespecawhite'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and the following botanical description were grown in 12-cm containers during the spring and summer for about 20 weeks in a glass-covered greenhouse and under conditions that closely approximate commercial production conditions in Südlohn-Oeding, Germany. During the production of the plants, day temperatures were about 20 to 25° C., night temperatures were about 16 to 18° C. and light levels ranged from 3,000 to 50,000 lux.

Botanical classification: *Petunia×hybrida* cultivar Wespecawhite.

Parentage:

*Female parent.*—Proprietary *Petunia×hybrida* selection identified as code number 98K6384-340, not patented.

*Male parent.*—Proprietary *Petunia×hybrida* selection identified as code number 98P040, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Numerous, fine, fibrous and well-branched.

Plant description:

*Form:*—Annual flowering plant; upright and outwardly spreading plant habit. Plants roughly spherical in shape. Viscid, glandular pubescent. Freely and continuous basal branching with lateral branches potentially forming at every node.

*Usage.*—Appropriate for hanging baskets, window boxes and patio containers.

*Plant height (from soil level to top of plant plane).*—About 18 cm.

*Plant diameter.*—About 50 to 60 cm.

*Stem description.*—Main branches, length: About 73 cm. Main branches, diameter: About 3.6 mm. Lateral branches, length: About 33 cm. Lateral branches, diameter: About 2 mm. Internode length: About 2.4 cm. Texture: Densely pubescent. Color: 144A.

*Foliage description.*—Arrangement: Alternate; simple. Length: About 3.9 cm. Width: About 2.3 cm. Shape: Ovate. Apex: Rounded. Base: Attenuate. Margin: Entire. Aspect: Flat. Texture, upper and lower surfaces: Leathery, pubescent. Venation pattern: Pinnate. Color: Developing foliage, upper surface: 137A. Developing foliage, lower surface: 146B. Fully expanded foliage, upper surface: 146A. Fully expanded foliage, lower surface: 146B. Venation, upper and lower surfaces: 146D. Petiole length: Less than 1 mm. Petiole diameter: About 2 to 5 mm. Petiole color: 146D.

Flower description:

*Flower type and habit.*—Single salverform flowers; flowers face upward and outward; single, axillary. Freely flowering habit.

*Natural flowering season.*—Long-day responsive; flowering from April until frost in the autumn in Germany; flowering continuous during this period.

*Fragrance.*—None detected.

*Flowering longevity on the plant.*—About one week.

*Flower size.*—Diameter: About 4.8 cm. Depth (height): About 3 cm. Tube length: About 2.7 cm. Throat diameter, distal end: About 1 cm. Tube diameter, proximal end: About 3 mm.

*Flower buds.*—Length: About 3.2 cm. Diameter: About 5 mm. Shape: Oblong. Color, towards, apex: 145D; veins 79A. Color, midsection: 144D; veins 79A. Color, base: 144D.

*Petals.*—Arrangement/appearance: Single whorls of five petals, fused into a flared trumpet. Length from throat: About 1.9 cm. Width: About 2.2 cm. Shape: Obtuse. Apex: Obtuse. Margin: Entire. Texture, upper and lower surfaces: Smooth, dull. Color: When opening and fully opened, upper surface: N155D with blush of N82B; color becoming closer to N155D with blush of N82C to N82D. When opening and fully opened, lower surface: N155D with random spots of N82B. Flower throat (inside): N155D. Flower tube (outside): N155D. Venation, upper surface: 83A, venation most pronounced towards center of flower. Venation, lower surface: Primary veins, 146D; secondary veins, 83A. Venation, throat: 83A. Venation, tube: Primary veins, 146D; secondary veins, 83A.

*Sepals.*—Arrangement/appearance: Single whorl of five sepals, fused at base; star-shaped. Length: About 1.2 cm. Width: About 2 mm. Shape: Linear. Apex: Obtuse. Margin: Entire. Texture, upper and lower surfaces: Dull, pubescent. Color, upper surfaces: 137A. Color, lower surfaces: 137B.

*Peduncles.*—Length: About 2.7 cm. Width: About 8 mm. Strength: Wiry, strong. Texture: Pubescent. Color: 146A.

*Reproductive organs.*—Stamens: Quantity: About five per flower. Anther shape: Four-parted, ovate. Anther length: About 2.5 mm. Anther width: About 1.8 mm. Anther color: 85D with overtones of 148D. Pollen amount: Abundant. Pollen color: 122B. Pistils: Quantity: One per flower. Pistil length: About 2 cm. Stigma shape: Square. Stigma color, immature: 144A. Stigma color, mature: 147A. Style length: About 1.5 cm. Style color: 145B to 145C. Ovary color: 145A. Seed/fruit: Seed and fruit production have not been observed.

Disease/pest resistance: Plants of the new *Petunia* have not been noted to be resistant to pathogens or pests common to *Petunia*.

Temperature tolerance: Plants of the new *Petunia* have been observed to be tolerant to temperatures from 2 to 30° C.

It is claimed:

1. A new and distinct cultivar of *Petunia* plant named 'Wespecawhite', as illustrated and described.

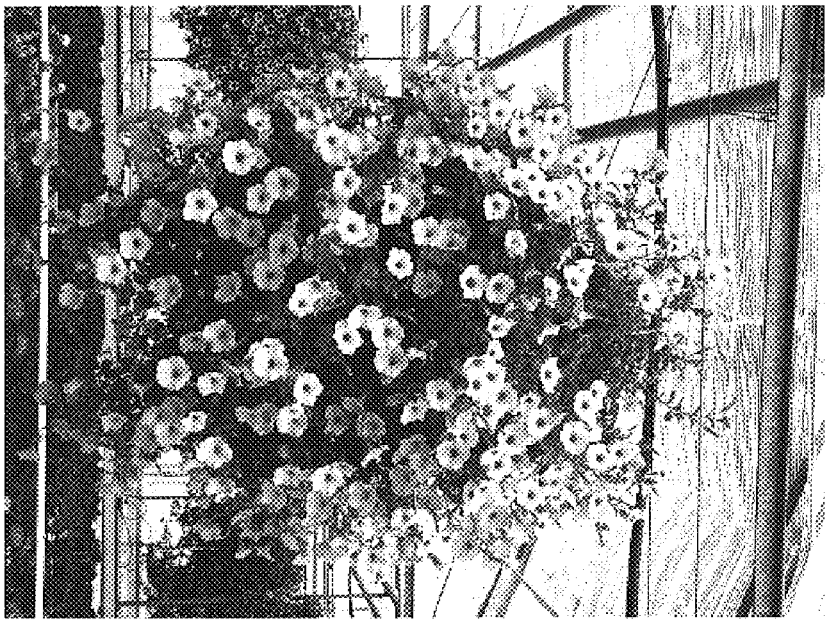
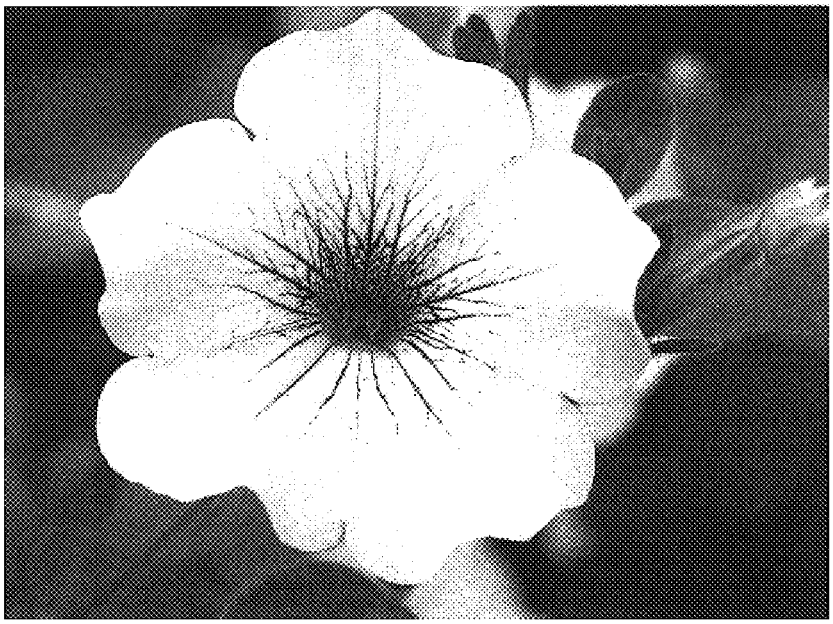

* * * * *